United States Patent [19]

Bauer et al.

[11] Patent Number: 5,071,464
[45] Date of Patent: Dec. 10, 1991

[54] HERBICIDAL AGENTS

[75] Inventors: Klaus Bauer, Rodgau; Hermann Bieringer, Eppstein/Taunus; Erwin Hacker, Hochheim am Main, all of Fed. Rep. of Germany

[73] Assignee: Hoechst Aktiengesellschaft, Frankfurt, Fed. Rep. of Germany

[21] Appl. No.: 500,736

[22] Filed: Mar. 28, 1990

Related U.S. Application Data

[63] Continuation of Ser. No. 728,815, Apr. 30, 1985, abandoned.

[30] Foreign Application Priority Data

May 2, 1984 [DE] Fed. Rep. of Germany ....... 3416201

[51] Int. Cl.$^5$ .................. A01N 57/00; A01N 43/48
[52] U.S. Cl. ............................................. 71/86; 71/92
[58] Field of Search ........................................ 71/86, 92

[56] References Cited

U.S. PATENT DOCUMENTS

| 4,188,487 | 2/1980 | Los ........................................ 71/92 |
| 4,349,506 | 7/1983 | Levitt ..................................... 71/92 |
| 4,594,098 | 6/1986 | Bauer et al. ............................ 71/86 |

FOREIGN PATENT DOCUMENTS

| 1160468 | 1/1984 | Canada ................................. 71/7.5 |
| 1160468 | 1/1984 | Canada ................................. 71/86 |
| 0106114 | 4/1984 | European Pat. Off. ................ 71/86 |

OTHER PUBLICATIONS

Los; Chem. Abstract; "Substituted Imidazolinyl Niotec Acids, Ester and Salts . . .", vol. 96, 199687q.

Colby, S. R., Calculating Synergistic And Antagonistic Responses Of Herbicide Combinations, *Weeds*, 15, 20–22 (1967).

Holm, L. G., "The World's Worst Weeds: Distribution And Biology," University Press of Hawaii, 32–40 and 105–113.

Richardson, W. G. et al., The Activity and Pre-Emergence Selectivity of Some Recently Developed Herbicides, *Weed Research Organization (Technical Report No. 62)*, 1–5 and 44–46 (England Feb. 1981).

Flint, J. L. et al., *Weed Technology*, 2,304–309 (1988).

*Primary Examiner*—Alan Siegel
*Assistant Examiner*—Jessica H. Nguyen
*Attorney, Agent, or Firm*—Curtis, Morris & Safford

[57] ABSTRACT

Combinations of herbicides of the formula I $$\begin{array}{c} CH_3 \quad O \\ \diagdown \; \| \\ P-CH-COOR \\ \diagup \quad | \\ CH_3 \quad OH \end{array} \qquad (I)$$

in which R denotes H or (substituted)alkyl, or salts thereof, together with herbicides of the Phosphinothricin type or together with herbicides of the Glyophosate type or together with (substituted) phenoxycarboxylic acids or together with herbicidal urea compounds or together with herbicidal triazine or together with certain herbicidal sulfonyl ureas or together with a compound of the formula VIII (VIII)

[structure: benzene ring fused with imidazolinone system bearing H$_3$C, CH(CH$_3$)$_2$, =O, N, NH substituents and COOH group]

or salts thereof, possess surprising synergistic properties and can be employed advantageously for the control of weeds in crops of useful plants or on areas used for industry.

7 Claims, No Drawings

HERBICIDAL AGENTS

This application is a continuation of application Ser. No. 06/728,815, filed Apr. 30, 1985 now abandoned.

The present invention relates to herbicidal agents which contain an active compound of the formula I

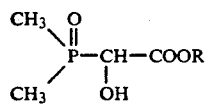

in which R denotes hydrogen or alkyl which is optionally monosubstituted or polysubstituted by halogen, hydroxyl, $(C_1-C_4)$-alkoxy or $(C_1-C_4)$-alkoxycarbonyl or salts thereof, in combination with a compound of the formula II

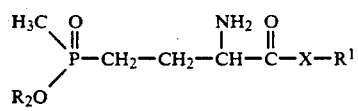

in which X denotes O or NH, and, in the event that X is O, $R^1$ denotes hydrogen, $(C_1-C_4)$-alkyl, optionally substituted ammonium or a metal cation, and, in the event that X is NH, $R^1$ denotes the radical —CH(CH$_3$)—CONH—CH(CH$_3$)—COOH and salts thereof, and, irrespective of the meaning of X, $R^2$ denotes hydrogen, optionally substituted ammonium or a metal cation, or acid addition salts thereof, or in combination with a compound of the formula III

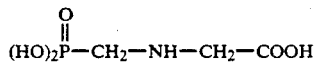

or salts and ester compounds thereof, or in combination with a compound of the formula IV

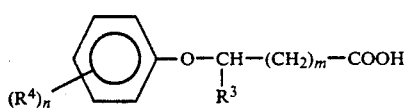

in which $R^3$ denotes H or methyl, the $R^4$s, whether identical or different, denote methyl or chlorine, n denotes the number 2 or 3 and m denotes the number 0 or 2, or salts and ester compounds thereof, or in combination with a compound of the formula V

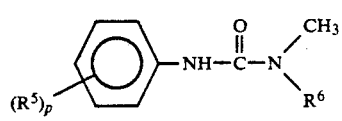

in which the $R^5$s, whether identical or different, denote chlorine, bromine, methyl or methoxy, $R^6$ denotes methyl or methoxy and p denotes the number 1 or 2, or in combination with a compound of the formula VI

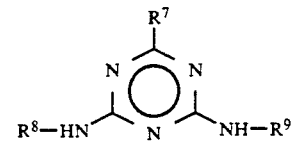

in which $R^7$ denotes chlorine, methylthio or methoxy, and $R^8$ and $R^9$ independently of one another denote $(C_1-C_4)$-alkyl, or in combination with a compound of the formula VII

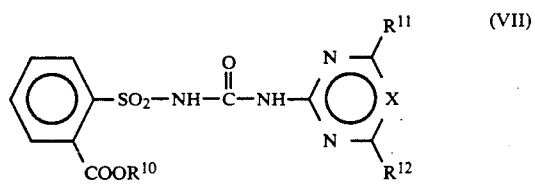

in which $R^{10}$ denotes $(C_1-C_4)$-alkyl, $R^{11}$ and $R^{12}$ independently of one another denote $(C_1-C_2)$-alkyl or $(C_1-C_2)$-alkoxy and X denotes CH or N, or in combination with a compound of the formula VIII or salts thereof.

The compounds of the formula I are described in German Offenlegungsschrift 3,238,958. They possess a systemic herbicidal action. On combining the compounds of the formula I with one of the compounds of the formulae II to VIII, a remarkable synergistic increase in action was found, surprisingly. In addition, an unexpected increase in the speed of action was observed.

Examples of suitable salts of the compounds of the formula I, derived from the free acid by replacing R=H by a cation, are: the alkali metal and alkaline earth metal salts, salts with ammonium or phosphonium, each of which can be mono-, di-, tri- or tetra-substituted, suitable substituents being alkyl, in particular $(C_1-C_{20})$-alkyl, phenyl, benzyl or hetero-aryl, of which particularly pyridyl and pyrimidinyl, all of which can be substituted by hydroxyl, $(C_1-C_4)$-alkoxy, $(C_1-C_4)$-alkylthio, mono-$(C_1-C_4)$-alkylamino or di-$(C_1-C_4)$-alkylamino, or trialkylsulphonium or trialkylsulfoxonium salts. The formula I embraces all the stereoisomers (L-forms and D-forms).

The following of the compounds of the formula I should be mentioned as particularly preferred: the free acid (R=H, compound Ia), the methyl ester (compound Ib, R=CH$_3$) and the sodium or ammonium salt of compound Ia (compound Ic, R=Na or NH$_4$).

The compounds of the formula II are described in U.S. Pat. No. 4,168,936 and in U.S. Pat. No. 4,309,208. In this respect, the formula II embraces both the racemic compounds and all the optical isomers. Thus the compound of the formula I in which $R^1$=H, alkyl or a cation can exist as the L-form or D-form. If $R^1$=—CH(CH$_3$)—CONH—CH(CH$_3$)—COOH, further optical isomers are possible. Suitable substituents for ammonium are those mentioned for the compound of the formula I. Metal ions which should be mentioned are primarily the alkali metal and alkaline earth metal ions, such as Na, K, Mg or Ca ions. Examples of salts suitable for the radical $R_1=CH(CH_3)-CONH-CH(CH_3)-COOH$ are the alkali or alkaline earth metal salts or the abovementioned ammonium salts, especially the sodium salts. Suitable acid addition salts are salts with inorganic acids, such as HCl, HBr, $H_2SO_4$ or $H_3PO_4$, and salts with organic acids, such as $(C_1-C_4)$-carboxylic acids, chlorinated acetic acids, tartaric acid or citric acid.

Compounds of the formula II which should be mentioned as preferred are the monoammonium salt (compound IIa, $R^1=H$, $R^2=NH_4$ and $X=O$), the free acid, known by the name Phosphinothricin, (compound IIb, $R^1$ and $R^2=H$, $X=O$) and the hydrochloride addition salt thereof (with 1 mole of HCl) or the Na or K salts ($R^1$ and $R^2=Na$, or K, $X=O$). Compound IIa is particularly preferred.

The compound of the formula III is known by the name Glyphosate. It can exist in the form of its salts, the isopropylammonium salt (compound IIIa) being particularly important. Further examples of suitable salts are metal salts, such as alkali and alkaline earth metal salts, optionally substituted phosphonium or ammonium salts, and sulphonium or sulfoxonium salts, for example trialkylsulfoxonium salts such as, in particular, the trimethylsulfoxonium salt. Esters which are of interest are, in particular, $(C_1-C_4)$-alkyl esters. Suitable substituents for ammonium and phosphonium are the radicals mentioned for the compounds of the formula I.

The following should be mentioned as examples of salts for the compounds of the formula IV: the alkali and alkaline earth metal salts and optionally substituted (for substituents see under formula I) ammonium salts. Suitable esters are, in particular, the $(C_1-C_8)$-alkyl esters or the allyl esters.

The following compounds of the formula IV should be mentioned particularly: 2,4-D (2,4-dichlorophenoxyacetic acid, compound Iva), Butoxone (2,4,5-trichlorophenoxyacetic acid), MCPA (2-methyl-4-chlorophenoxyacetic acid, compound Ivb), MCPP [2-(2-methyl-4-chlorophenoxy)-propionic acid, compound Ivc], dichloroprop-[2-(2,4-dichlorophenoxy)-propionic acid] or MCPB [4-(4-chloro-2-methylphenoxy)-butyric acid] or salts and esters thereof.

Compounds of the formula V which are employed are, in particular, the compounds diuron (N-3,4-dichlorophenyl-N',N'-dimethylurea) and linuron (N-3,4-dichlorophenyl-N'-methoxy-N'-methylurea).

The following are preferred amongst the compounds of the formula VI: atrazine (2-ethylamino-4-chloro-6-isopropylamino-s-triazine), simazine (4,6-bis-ethylamino-2-chloro-s-triazine), terbuthylazine (6-ethylamino-2-tert.butylamino-4-chloro-s-triazine), ametryn (2-ethylamino-4-isopropylamino-6-methylthio-s-triazine) and prometryn (2,4-bis-isopropylamino-6-methylthio-s-triazine).

Amongst the compounds of the formula VII, the compound in which $R^{10}$, $R^{11}$ and $R^{12}=CH_3$ and $X=CH$ is of particular interest; this compound is known by the name Sulfometuron-methyl.

All the conventional salts, such as alkali metal salts or optionally substituted ammonium salts, especially the isopropylammonium salt, are suitable for the compounds of the formula VIII. Formula VIII embraces all the stereoisomers.

The present invention also relates to threefold combinations of compounds of the formula I containing two different active compounds of the formulae II to VIII.

The active compound combinations according to the invention cover a broad weed spectrum. They are suitable, for example, for the control of annual and perennial weeds, such as, for example, Agropyron, Paspalum, Cynodon, Imperata, Pennisetum, Convolvulus, Cinium, Rumex and others.

The combinations according to the invention can be employed for the selective control of weeds in plantation crops, such as oil palms, coconut palms, rubber trees, citrus, pineapples, cotton, coffee, cocoa and others, and also in the cultivation of fruit and vines. The combinations according to the invention can also be employed in agriculture using the so-called "no till" or "zero till" method. They can, however, also be used non-selectively on paths, grounds, industrial plants etc., in order to keep these areas free from undesirable plant growth.

The mixing ratios of the compounds of the formula I to the compounds of the formulae II, III, IV, V, VI, VII or VIII can vary within wide limits, especially between about 80:1 and 1:10. The choice of the mixing ratio depends on various parameters, such as the nature of the components in the mixture, the stage of development of the weeds and the weed spectrum. It is preferable to select mixing ratios between 40:1 and 1:5.

The combinations according to the invention can be in the form of mixed formulations—wettable powders or emulsion concentrates—which are then applied, diluted with water, in a conventional manner; they can, however, also be prepared as so-called tank mixtures by the combined dilution with water of the separately formulated components.

The application rates of the herbicide of the formula I in the mixtures of active compounds vary, in general, between 0.5 and 4.0 kg/hectare, whereas the application rates of the compounds of the formulae II to VIII can be within the range between 0.01 and 5.0 kg/hectare, in particular for:

compounds of the formula II between 0.1 and 2.0 kg of active ingredient/hectare, compounds of the formula III between 0.1 and 2.0 kg of active ingredient/hectare, compounds of the formula IV between 0.1 and 2.0 kg of active ingredient/hectare, compounds of the formula V between 0.1 and 2.0 kg of active ingredient/hectare, compounds of the formula VI between 0.5 and 5.0 kg of active ingredient/hectare, compounds of the formula VII between 0.01 and 0.5 kg of active ingredient/hectare, and compounds of the formula VIII between 0.01 and 0.5 kg of active ingredient/hectare.

The agents according to the invention can be put on the market in the conventional preparations with which those skilled in the art are familiar, for example in the form of wettable powders, dusting agents, granules, dispersion concentrates, emulsifiable concentrates or sprayable solutions. The agents formulated in this way generally contain the active compounds in concentrations of 2 to 95% by weight.

Wettable powders are preparations which can be dispersed uniformly in water and which, besides the active compounds, also contain not only a diluent or inert material but also wetting agents, for example polyoxethylated alkylphenols, polyoxethylated oleylamines or stearylamines, alkylsulfonates or alkylphenylsulfonates, and dispersing agents, for example sodium ligninsulfonate, sodium dinaphthylmethanedisulfonate or sodium oleylmethyltauride.

Emulsifiable concentrates are obtained by dissolving the mixture of active compounds in an organic solvent, for example butanol, cyclohexanone, dimethylformamide, xylene or aromatic compounds of fairly high boiling point, and adding a nonionic wetting agent, for example a polyoxethylated alkylphenol or a polyoxethylated oleylamine or stearylamine.

The total concentration of active compound in wettable powders varies between about 10% and 95%, the remainder being composed of the formulation additives indicated above. In emulsifiable concentrates the concentration of active compound is about 10% to 80%. Formulations in the form of dust in most cases contain 5% to 20% of active compounds, while sprayable solutions contain about 2% to 20%. In the case of granules, the content of active compound depends in part on the form (liquid or solid) in which the active compounds are present and on the granulating auxiliaries, fillers etc. which are used.

For application, the commercially available concentrates are, if appropriate, diluted in a conventional manner, for example with water in the case of wettable powders and emulsifiable concentrates.

The preparations in the form of dusts and granules and also sprayable solutions are not diluted further with other inert materials before application.

A. Examples of Formulations a) A dusting agent is obtained by mixing 10 parts by weight of a mixture of active compounds and 90 parts by weight of talc as an inert material and comminuting the mixture in a beater mill.

b) A wettable powder which is readily dispersible in water is obtained by mixing 25 parts by weight of a mixture of active compounds, 64 parts by weight of kaolin-containing quartz as an inert material, 10 parts by weight of potassium ligninsulfonate and 1 part by weight of sodium oleoylmethyltauride as a wetting and dispersing agent, and grinding the mixture in a pinned disk mill.

c) A dispersion concentrate which is readily dispersible in water is obtained by mixing 20 parts by weight of a mixture of active compounds with 6 parts by weight of an alkylphenol polyglycol ether (®Triton×207), 3 parts by weight of isotridecanolpolyglycol ether (8 EO) and 71 parts by weight of paraffinic mineral oil (boiling range, for example, approx. 255° to over 377° C.), and grinding the mixture in a ball mill to a fineness of less than 5 microns.

d) An emulsifiable concentrate is obtained from 15 parts by weight of a mixture of active compounds, 75 parts by weight of cyclohexanone as a solvent and 10 parts by weight of oxethylated nonylphenol (10 EO) as an emulsifier.

B. Biological Examples

Proof of synergism in the examples which follow is afforded by comparing the additive degree of action calculated from the action of the individual components with the experimentally found degree of action of the combinations of active compounds. The additive degree of action is calculated by the formula of S. R. Colby (cf. Calculating synergistic and antagonistic responses of herbicide combinations, Weeds, 15, 1967, pages 20 to 22).

This formula is:

$$E = X + Y - \frac{X \cdot Y}{100}$$

where X denotes the % damage caused by herbicide A at an application rate of x kg/hectare, Y denotes the % damage caused by herbicide B at an application rate of y kg/hectare and E denotes the expected % damage caused by herbicides A+B at an application rate of x+y kg/hectare.

If the actual damage is greater than that calculated, the action of the combination of active compounds is more than additive, i.e. a synergistic effect is present. This is demonstrated by means of the biological examples in the tables below, where the additive action calculated from the above formula is quoted in brackets for the results of the treatments with combinations, in the right-hand columns.

EXAMPLE 1

Seeds of various gramineous weeds and weeds were sown in sandy loam soil in plastic pots (diameter 9 cm), and were cultivated for 3–4 weeks in a greenhouse under good conditions for growth. The compounds, formulated as aqueous solutions, were then sprayed onto the parts of the plants above ground, individually and also in combination, in the form of sprayable solutions. The amount of water used corresponded to 400 l/hectare.

The herbicidal action was assessed visually after a waiting period of approx. 3 weeks in the greenhouse under optimum conditions for growth.

The results show that the combination of active compounds enabled an unexpectedly high herbicidal effectiveness to be achieved, which is considerably better than could be expected on the basis of the sum of the individual action of the active compounds.

TABLE 1

| Herbicide | Dose, kg of active ingredient/ hectare | Herbicidal action, % AVF | Herbicidal action, % ALM |
|---|---|---|---|
| Ia | 0.25 | 5 | 0 |
| | 0.5 | 35 | 35 |
| | 1.0 | 45 | 78 |
| IIa | 0.125 | 5 | 15 |
| | 0.250 | 10 | 40 |
| Ia + IIa | 0.25 + 0.125 | 45(9.8) | 50(15) |
| | 0.50 + 0.125 | 70(38.2) | 70(44.7) |
| | 1.0 + 0.125 | 75(47.7) | 100(81) |
| | 0.25 + 0.25 | 65(14.5) | 50(40) |
| | 0.50 + 0.25 | 70(41.5) | 78(61) |
| | 1.0 + 0.25 | 83(50.5) | 98(87) |

Ia: compound of the formula 1 in which R = H
IIa: compound of the formula II in which $R^1$ = H, $R^2$ = $NH_4$ and X = O

EXAMPLE 2

Seeds of various gramineous weeds and weeds were sown in sandy loam soil in plastic pots (diameter 9 cm) and were cultivated for 3–4 weeks in a greenhouse under good conditions for growth. The compounds, formulated as wettable powders of aqueous solutions, were then sprayed onto the parts of the plants above ground, in the form of aqueous suspensions or sprayable solutions, respectively. The amount of water used corresponded to 300 l/hectare.

The herbicidal action was assessed 3 weeks after application. As shown in Table 2, the results indicate the extremely good effectiveness of the combination according to the invention.

TABLE 2

| Herbicide | Dose, kg of active ingredient/hectare | Herbicidal action, % | | |
|---|---|---|---|---|
| | | AVF | ALM | LOM |
| Ib | 0.25 | 15 | 40 | 35 |
| | 0.5 | 55 | 75 | 90 |
| IIIa | 0.25 | 55 | 70 | 75 |
| Ib + IIIa | 0.25 + 0.25 | 85(61.7) | 90(82) | 99(83.7) |
| | 0.5 + 0.25 | 97(71.7) | 99(92.5) | 100(97.5) |

Ib = compound of the formula I in which R = CH$_3$
IIIa = isopropylammonium salt of the compound of the formula III
AVF = *Avena fatua*
ALM = *Alopecurus myosuroides*
LOM = *Lolium multiflorum*

EXAMPLE 3

Rhizome or pieces of root of various weeds were sown in sandy loam soil in pots of diameter 13 cm and were cultivated in a greenhouse until sideshoots developed. The combinations according to the invention, formulated as aqueous solutions or as emulsion concentrates, were sprayed onto the green parts of the test plants above ground at a rate of 400 l/hectare. The results were assessed after 14 days.

The results demonstrate the strong synergistic action of the combinations against perennial weeds such as Cynodon dactylon (CND), Agropyron repens (AGR) and Cyperus esculentus (CYE) (see Table 3).

EXAMPLE 4

The compounds were applied individually and in combination, by the same method as in Example 3, to perennial weeds which had sent out sideshoots. The results of assessment in Table 4, obtained 43 days after treatment, once again demonstrate the synergistic action of the combination.

EXAMPLE 5

The compounds were applied individually and in combination, by the same method as in Example 3, to perennial grasses at the sideshoot stage. The results were assessed 6 weeks later (Table 5). This made it evident that the herbicide combinations according to the invention lead to an unexpectedly high synergistic increase in the long-term action.

TABLE 3

| Product | Dose, kg of active ingredient/hectare | Herbicidal action, % | | |
|---|---|---|---|---|
| | | CND | AGR | CYE |
| IIa | 0.25 | 50 | 60 | 20 |
| Ia | 4.0 | 75 | 50 | — |
| | 2.0 | 70 | 40 | — |
| | 1.0 | 60 | 30 | — |
| | 0.5 | 30 | 20 | — |
| Ia + IIa | 4.0 + 0.25 | 95(87.5) | 95(80) | — |
| | 2.0 + 0.25 | 95(85) | 90(76) | — |
| | 1.0 + 0.25 | 90(80) | 85(72) | — |
| | 0.5 + 0.25 | 90(65) | 75(68) | — |
| Ic | 4.0 | 80 | 40 | 40 |
| | 2.0 | 60 | 30 | 15 |
| | 1.0 | 30 | 15 | 0 |
| | 0.5 | 20 | 10 | 0 |
| Ic + IIa | 4.0 + 0.25 | 98(90) | 96(86) | 60(52) |
| | 2.0 + 0.25 | 98(80) | 95(72) | 40(32) |

TABLE 3-continued

| Product | Dose, kg of active ingredient/hectare | Herbicidal action, % | | |
|---|---|---|---|---|
| | | CND | AGR | CYE |
| | 1.0 + 0.25 | 97(65) | 90(66) | 40(20) |
| | 0.5 + 0.25 | 95(60) | 90(64) | 35(20) |
| Ib | 4.0 | 55 | 35 | — |
| | 2.0 | 50 | 25 | — |
| | 1.0 | 45 | 20 | — |
| | 0.5 | 40 | 20 | — |
| Ib + IIa | 4.0 + 0.25 | 95(77) | 85(74) | — |
| | 2.0 + 0.25 | 90(75) | 80(70) | — |
| | 1.0 + 0.25 | 90(72.5) | 70(68) | — |
| | 0.5 + 0.25 | 80(70) | 60(68) | — |

Ic = Na salt of the compound Ia (R = Na)

TABLE 4

| Product | Dose, kg of active ingredient/hectare | Herbicidal action, % | | |
|---|---|---|---|---|
| | | CND | AGR | CYE |
| IIIa | 0.25 | 65 | 58 | 63 |
| Ia | 0.5 | 78 | 33 | 35 |
| | 0.25 | 43 | 5 | 18 |
| Ia + IIIa | 0.5 + 0.25 | 98(92) | 86(72) | 83(76) |
| | 0.25 + 0.25 | 85(81) | 75(60) | 80(70) |

TABLE 5

| Product | Dose, kg of active ingredient/hectare | Herbicidal action, % | |
|---|---|---|---|
| | | AGR | CND |
| Ib | 1.0 | 65 | 40 |
| | 0.5 | 30 | 30 |
| Atrazine | 1.0 | 42 | 30 |
| | 0.5 | 20 | 5 |
| Diuron | 1.0 | 35 | 40 |
| | 0.5 | 15 | 10 |
| Ib + Atrazine | 0.5 + 0.5 | 85(44) | 75(33) |
| | 1.0 + 0.5 | 95(72) | 90(43) |
| | 0.5 + 1.0 | 90(59) | 95(51) |
| Ib + Diuron | 0.5 + 0.5 | 80(40) | 75(37) |
| | 1.0 + 0.5 | 93(70) | 90(46) |
| | 0.5 + 1.0 | 85(45) | 90(58) |

Atrazine = 2-ethylamino-4-chloro-6-isopropylamin-s-triazine
Diuron = N-3,4-dichlorophenyl-N',N'-dimethylurea

EXAMPLE 6

Seeds of various gramineous weeds and weeds were sown in sandy loam soil in plastic pots of diameter 9 cm and were cultivated for 3-4 weeks in a greenhouse under good conditions for growth. The compounds, formulated as wettable powders, emulsion concentrates or aqueous solutions, were then sprayed onto the parts of the plants above ground, in the form of aqueous suspensions, emulsions or sprayable solutions, respectively. The amount of water used corresponded to the equivalent of 600 l/hectare.

The herbicidal action was assessed visually 3 weeks after the application by comparison with untreated controls. As shown in Table 6, the results indicate the extremely good effectiveness of the combination according to the invention and its superiority over the individual active compounds, particularly in the case of the monocotyledonous species of weeds.

TABLE 6

| Herbicide | Dose, kg of active ingredient/hectare | Herbicidal action, % | |
|---|---|---|---|
| | | AVF | ALM |
| Ia | 1 | 83 | 75 |
| | 0.5 | 30 | 25 |

TABLE 6-continued

| Herbicide | Dose, kg of active ingredient/hectare | Herbicidal action, % | |
|---|---|---|---|
| | | AVF | ALM |
| | 0.25 | 15 | 20 |
| Iva | 0.5 | 15 | 20 |
| | 0.25 | 10 | 0 |
| Ivb | 0.5 | 5 | 30 |
| | 0.25 | 0 | 10 |
| Ivc | 0.5 | 15 | 35 |
| | 0.25 | 10 | 15 |
| Ia + Iva | 1 + 0.5 | 90(85) | 95(80) |
| | 0.5 + 0.5 | 50(40) | 50(40) |
| | 0.25 + 0.5 | 40(27) | 40(36) |
| Ia + Iva | 1 + 0.25 | 85(84) | 93(75) |
| | 0.5 + 0.25 | 65(37) | 75(25) |
| | 0.25 + 0.25 | 25(23) | 40(20) |
| Ia + Ivb | 1 + 0.5 | 97(84) | 98(80) |
| | 0.5 + 0.5 | 55(34) | 78(47) |
| | 0.25 + 0.5 | 35(20) | 30(44) |
| Ia + Ivb | 1 + 0.25 | 94(83) | 93(78) |
| | 0.5 + 0.25 | 65(30) | 60(33) |
| | 0.25 + 0.25 | 25(15) | 30(28) |
| Ia + IVc | 1 + 0.5 | 94(85) | 89(83) |
| | 0.5 + 0.5 | 60(40) | 70(51) |
| | 0.25 + 0.5 | 30(28) | 30(48) |
| 4 | 1 + 0.25 | 90(84) | 80(79) |
| Ia + Ivc | 0.25 + 0.25 | 45(37) | 50(36) |
| | 0.125 + 0.25 | 30(23) | 40(32) |

Iva: compound of the formula IV in which $R_3$ = H and $(R_4)_n$ = 2,4-Cl; m = O
Ivb: compound of the formula IV in which $R_3$ = H and $(R_4)_n$ = 2-$CH_3$ and 4-Cl; m = O
Ivc: compound of the formula IV in which $R_3$ = $CH_3$ and $(R_4)_n$ = 2-$CH_3$ and 4-Cl; m = O.

EXAMPLE 7

According to Example 6 annual mono- and dicotyledonous species of weeds were treated with the single components and with the combinations of the invention.

As shown in Table 7 the inventive combinations possess also in case of the components VII and VIII superior synergistic herbicidal efficiencies in comparison to the single components.

TABLE 7

| herbicide | Dose kg a.i./ha | herbicidal action, % | | |
|---|---|---|---|---|
| | | AVF | ECG | CRS |
| Ia | 0,5 | 60 | 70 | 80 |
| | 0,25 | 10 | 25 | 60 |
| | 0,125 | 0 | 10 | 10 |
| VIIa | 0,006 | 50 | 70 | — |
| VIIIa | 0,015 | 60 | 30 | 60 |
| Ia + VIIa | 0,5 + 0,006 | 90(80) | 100(91) | — |
| | 0,25 + 0,006 | 80(55) | 98(78) | — |
| | 0,125 + 0,006 | 70(50) | 90(73) | — |
| Ia + VIIIa | 0,5 + 0,015 | 90(84) | 100(79) | 99(92) |
| | 0,25 + 0,015 | 85(64) | 99(48) | 95(84) |
| | 0,125 + 0,015 | 75(60) | 70(37) | 90(64) |

VIIa: Compound of the formula VII in which $R_{10}$, $R_{11}$, $R_{12}$ = $CH_3$
VIIIa: Isopropylammonium salt of the compound of formula VIII
AVF = *Avena fatua*
ECG: *Echinochloa crus galli*
CRS = *Chrysanthemum segetum*

We claim:

1. A herbicidal agent which contains an active compound of formula I

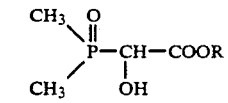

in which R is hydrogen or ($C_1$-$C_4$)-alkyl, or a salt thereof derived from the free acid, in combination with a compound of formula VIII

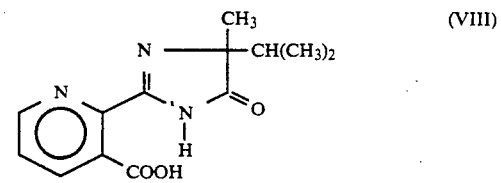

or a salt thereof, wherein the ratio by weight of compound of formula I to compound of formula VIII is 40:1 to 8:1.

2. A herbicidal agent as claimed in claim 1 wherein the application rate of the compound of formula I is 0.125 to 2.0 kg a.i./ha and the application rate of the compound of formula VIII in the combination is 0.001 to 0.5 kg a.i./ha.

3. A herbicidal agent as claimed in claim 1 wherein the application rate of the compound of formula I is 0.25 to 0.5 kg a.i./ha and the application rate of the compound of formula VIII in the combination is 0.003 to 0.015 kg a.i./ha.

4. A herbicidal agent as claimed in claim 1 wherein R in formula I is hydrogen.

5. A herbicidal agent as claimed in claim 1 wherein the compound of formula VIII is the isopropylammonium salt of the free acid of the formula VIII.

6. A process for controlling weeds which comprises applying an effective amount of the herbicidal agent of claim 1 to a cultivated area where said weeds are growing.

7. A process for controlling weeds of the variety Avenua fatua, Echinochloa crus galli and Chrysanthemum segetum which comprises applying an effective amount of the herbicidal agent of claim 4 to a cultivated area where said weeds are growing.

* * * * *